United States Patent [19]
Jamas et al.

[11] Patent Number: 5,532,223
[45] Date of Patent: Jul. 2, 1996

[54] USE OF AQUEOUS SOLUBLE GLUCAN PREPARATIONS TO STIMULATE PLATELET PRODUCTION

[75] Inventors: Spiros Jamas, Boston; D. Davidson Easson, Jr., Shrewsbury; Gary R. Ostroff, Worcester, all of Mass.

[73] Assignee: Alpha-Beta Technology, Inc., Worcester, Mass.

[*] Notice: The term of this patent shall not extend beyond the expiration date of Pat. No. 5,488,040.

[21] Appl. No.: 452,971

[22] Filed: May 30, 1995

Related U.S. Application Data

[63] Continuation of Ser. No. 60,418, May 11, 1993, Pat. No. 5,488,040, which is a continuation-in-part of Ser. No. 934,015, Aug. 21, 1992, and Ser. No. 855,578, Mar. 23, 1992, abandoned, which is a continuation-in-part of Ser. No. 838,288, May 5, 1992, abandoned, which is a continuation of PCT/US90/05041, Sep. 6, 1990, which is a continuation-in-part of Ser. No. 404,738, Sep. 8, 1989, abandoned.

[51] Int. Cl.$^6$ ................................. A61K 31/715
[52] U.S. Cl. .................. 514/54; 536/123.12; 536/123.1; 536/124
[58] Field of Search ......................... 514/54; 536/123.12, 536/123.1, 124

[56] References Cited

U.S. PATENT DOCUMENTS

| | | | |
|---|---|---|---|
| 4,138,479 | 2/1979 | Truscheit et al. | 424/88 |
| 4,237,266 | 12/1980 | Sugiura et al. | 536/1.11 |
| 4,707,471 | 11/1987 | Larm et al. | 514/54 |
| 4,739,046 | 4/1988 | DiLuzio et al. | 536/124 |
| 4,761,402 | 8/1988 | Williams et al. | 514/54 |
| 4,810,646 | 3/1989 | Jamas et al. | 536/123 |
| 5,057,503 | 10/1991 | Czop et al. | 514/54 |
| 5,234,908 | 8/1993 | Szabo et al. | 514/21 |
| 5,322,841 | 6/1994 | Jamas et al. | 514/54 |

FOREIGN PATENT DOCUMENTS

| | | |
|---|---|---|
| 0463540 | 1/1992 | European Pat. Off. |
| 55-071701 | 8/1980 | Japan |
| 56-076401 | 9/1981 | Japan |
| 59-045301 | 6/1984 | Japan |
| 59-210901 | 4/1985 | Japan |
| 2076418 | 12/1981 | United Kingdom |
| 91/03248 | 3/1991 | WIPO |
| 91/03495 | 3/1991 | WIPO |
| 92/13896 | 8/1992 | WIPO |
| 94/03498 | 2/1994 | WIPO |
| 94/03500 | 2/1994 | WIPO |

OTHER PUBLICATIONS

Tumori, vol. 74, issued 1988, Lerza et al, "Studies on Hemotoxicity of Cyclophosphamide, Doxorubicin and Cis--Diamminodichloroplatinum Combined with Sodium-2-Mercaptoethane Sulfonate", see pp. 333–337.

Cancer Research, vol. 52, issued 01 Aug. 1992, Damia et al, "Prevention of Acute Chemotherapy–Induced Death in Mice by Recombinant Human Interleukin 1: Protection from Hematological and Nonhematological Toxicities", see pp. 4082–4089.

Cancer Research, vol. 44, issued Sep. 1984, Evans et al, "Modification of the Bone Marrow Toxicity of Cis–Diamminedichloroplatinum(II) in Mice by Diethyldithiocarbamate", see pp. 3686–3690.

Cancer Research, vol. 54, issued 01 Feb. 1994, Green et al, "Preclinical Evaluation of WR–151327: An Orally Active Chemotherapy Protector", see pp. 738–741.

Cancer Letters, vol. 79, issued 1994, Yoshizawa et al, "Effects of Natural Human Interleukin–6 on Thrombopoiesis and Tumor Progression in Tumor–Bearing Mice", pp. 83–89.

Biotherapy, vol. 7, issued 1994, Patchen et al, "Mast Cell Growth Factor (C–kit Ligand) in Combination with Granulocyte–Macrophage Colony–Stimulating Factor and Interleukin–3: in vivo Hemopoietic effects in Irradiated Ice compared to in vivo effects", see pp. 13–26.

Experimental Hematology, vol. 21, issued 1993, Patchen et al, "Effects of Combined Administration of Interleukin–6 and Granulocyte Colony–Stimulating Factor on Recovery from Radiation–Induced Hemopoietic Aplasia", see pp. 338–344.

Seminars in Oncology, vol. 21, No. 5, issued Oct. 1994, "Granulocyte Colony–Stimulating Factor and Amifostine (Ethyol) Synergize to Enhance Hemopoietic Reconstitution and Increase Survival in Irradiated Animals" see pp. 26–32.

Janusz, M. J., et al., "Isolation of Soluble Yeast β–Glucan that Inhibit Human Monocyte Phagocytosis Mediated by β–Glucan Receptors," *J. Immunol.*, 137:3270–3276 (1986).

(List continued on next page.)

Primary Examiner—Douglas W. Robinson
Assistant Examiner—Everett White
Attorney, Agent, or Firm—Hamilton, Brook, Smith & Reynolds

[57] ABSTRACT

The present invention relates to neutral soluble β-glucans which exert potent and specific hematopoietic and immunological effects without stimulating the production of certain cytokines, to preparations containing the novel β-glucans, and to a novel manufacturing process therefor. The neutral soluble glucan preparation has a high affinity for the β-glucan receptor of human monocytes and retains two primary biological (or immunological) activities, (1) the enhancement of microbicidal activity of phagocytic cells, and (2) monocyte and neutrophil hemopoietic activity. Unlike soluble glucans described in the prior art, the neutral soluble glucan of this invention neither induces nor primes IL-1 and TNF production in vitro and in vivo. Safe and efficacious preparations of neutral soluble glucan of the present invention can be used in therapeutic and/or prophylactic treatment regimens of humans and animals to enhance their immune response, without stimulating the production of certain biochemical mediators (e.g., IL-1, TNF and leukotrienes) that can cause detrimental side effects, such as fever and inflammation.

32 Claims, 7 Drawing Sheets

OTHER PUBLICATIONS

Manners, D. J., et al., "The Structure of a β-(1→3)-D-Glucan from Yeast Cell Walls," *Biochem. J.*, 135:19–30 (1973).

Williams, D. L., et al., "Pre-clinical Safety Evaluation of Soluble Glucan," *Chemical Abstracts*, 109:66566q (1988).

Fleet, G. H., et al., "Isolation and Composition of an Alkali–Soluble Glucan from the Cell Walls of *Saccharomyces cerevisiae*," *Chemical Abstracts*, 85:89819z (1976).

Bacon, J., et al., "The Glucan Components of the Cell Wall of Baker's Yeast (*Saccharomyces cerevisiae*) Considered in Relation to its Ultrastructure," *Biochem. J.*, 114:557–567 (1969).

Vestnik Federalniho Uradu Pro Vynalezy, 10:111 (1989).

Vestnik Federalniho Uradu Pro Vynalezy, 11:122–123 (1989).

Onderdonk, A. B., et al., "Anti–Infective Effect of Poly–β1–6–Glucotrisyl–β1–3–Glucopyranose Glucan In Vivo," *Infec. Immun.*, 60:1642–1647 (1992).

Abel, G. and Czop, J. K., "Activation of Human Monocyte GM–CSF and TNF–α Production by Particulate Yeast Glucan," International Congress for Infectious Diseases, Montreal, Canada (Abstract), (1990).

Chihara, G., et al., "Lentinan as a Host Defense Potentiator (HPD)," *Int. J. Immunotherapy*, V(4):145–154 (1989).

Sherwood, E. R., et al., "Enhancement of Interleukin–1 and Interleukin–2 Production by Soluble Glucan," *Int. J. Immunopharmac.*, 9(3):261–267 (1987).

Williams, D. L., et al., "Pre-clinical Safety Evaluation of Soluble Glucan," *Int. J. Immunopharmac.*, 10(4):405–414 (1988).

Browder, W., et al., "Beneficial Effect of Enhanced Macrophage Function in the Trauma Patient," *Ann. Surg.*, 605–613 (1990).

Fleet, G. H., et al., "Isolation and Composition of an Alkali–soluble Glucan from the Cell Walls of *Saccharomyces cerevisiae*," *Journal of General Microbiology*, 94:180–192 (1976).

Miyazaki, T., et al., "Structural Examination of Antitumour, Water–Soluble Glucans from *Grifora umbellata* by Use of Four Types of Glucanase," *Carbohydrate Research*, 65:235–243 (1978).

Reiskind, J. B. and Mullins, J. T., "Molecular Architecture of the Hyphal Wall of *Achlya ambisexualis* Raper. II. Ultrastructural Analyses and a Proposed Model[1]," *J. Microbiol.*, 27:1100–1105 (1981).

Latge, J. P., et al., "Composition chimique et ultrastructure des parois des corps hyphaux et des azygospores de *Conidiobolus obscurus*," *J. Microbiol.*, 30:1507–1521 (1984).

Sherwood, E. R., et al., "Soluble Glucan and Lymphokine–activated Killer (LAK) Cells in the Therapy of Experimental Hepatic Metastases," *Chemical Abstracts*, 108:179752V (1988).

Hara, C., et al., "A Branched (1→3)-β-D-Glucan From a Water Extract of *Dictyophora indusiata* FISCH," *Carb. Res.*, 145:237–246 (1986).

Goldman, R., "Induction of a β–1,3–D–Glucan Receptor in P388D1 Cells Treated with Retinoic Acid of 1,25–dihydroxyvitamin $D_3$," *Immunology*, 63:319–324 (1988).

Konopski, Z., et al., "Phagocytosis of β–1,3–D–Glucan–Derivatized Microbeads by Mouse Peritoneal Macrophages Involves Three Different Receptors," *Scand. J. Immunol.*, 33:297–306 (1991).

Bacon, J. S. D., et al., "Glucan Components of the Cell Wall of Bakers' Yeast (*Saccharomyces cerevisiae*) Considered in Relation to its Ultrastructure," *Chemical Abstracts*, 71:109168c (1969).

Williams, D. L., et al., "Development of a Water–Soluble, Sulfated (1→3)-β-D-Glucan Biological Response Modifier Derived from *Saccharomyces cerevisiae*," *Carbohydrate Research*, 235:247–257 (1992).

Williams, D. L., et al., "A Sequential Multi–Assay Protocol for the Preclinical Assessment of Natural Product Complex Carbohydrate Immunomodulators," *Develop. Biol. Standard.*, 77:129–136 (1992).

Williams, D. L., et al., "Development, Physicochemical Characterization and Preclinical Efficacy Evaluation of a Water Soluble Glucan Sulfate Derived from *Saccharomyces cerevisiae*," *Immunopharmacology*, 22:139–156 (1991).

Pretus, H. A., et al., "Isolation, Physicochemical Characterization and Preclinical Efficacy Evaluation of Soluble Scleroglucan[1]," *The Journal of Pharmacology and Experimental Therapeutics*, 500–510 (1991).

Jamas et al., "A Novel Class of Macrophage–Activating Immunomodulators", ACS Symposium Series, *Polymeric Drugs and Delivery Systems*, Chapter 5, pp. 44–51 (1991).

Stashenko et al., "Reduction of Infection–Stimulated Periapical Bone Resorption by the Biological Response Modifier PGG Glucan", *J. Dent. Res.* 74(1):323–330 (1995).

Stashenko et al., "Inhibition of Periapical Bone Resorption by a Biological Response Modifier", *J. Dent. Res.* 73 (IADR Abstracts) No. 146 (1994).

Babineau et al., "Randomized Phase I/II Trial of a Macrophage–Specific Immunomodulator (PGG–Glucan) in High–Risk Surgical Patients", *Annals of Surgery* 220(5):601–609 (1994).

Babineau et al., "A Phase II Multicenter, Double–Blind Randomized, Placebo–Controlled Study of Three Dosages of an Immunomodulator (PGG–Glucan) in High Risk Surgical Patients", *Arch. Surg.* 129:1204–1210 (1994).

USE OF AQUEOUS SOLUBLE GLUCAN PREPARATIONS TO STIMULATE PLATELET PRODUCTION

RELATED APPLICATION

This application is a continuation of U.S. Ser. No. 08/060,418, filed May 11, 1993, now U.S. Pat. No. 5,488,040, which is a Continuation-in-Part of U.S. Ser. Nos. 07/934,015, filed Aug. 21, 1992 and 07/855,578, filed Mar. 23, 1992, now issued as U.S. Pat. No. 5,488,040, the disclosures of which are incorporated herein by reference, which is a Continuation-in-Part of U.S. Ser. No. 07/838,288, filed May 5, 1992, now abandoned, which is a 371 of PCT/US90/05041, filed Sep. 6, 1990, which is a Continuation-in-Part of U.S. Ser. No. 07/404,738, filed Sep. 8, 1989, now abandoned.

BACKGROUND OF THE INVENTION

In the early 1960's, zymosan, a crude insoluble yeast extract prepared by boiling yeast before and after trypsin treatment, was noted to produce marked hyperplasia and functional stimulation of the reticuloendothelial system in rodents. In animal studies, zymosan preparations were shown to inactivate complement component C3, to enhance antibody formation, to promote survival following irradiation, to increase resistance to bacterial infections, to inhibit tumor development, to promote graft rejection, and to inhibit dietary-induced hypercholesterolemia and cholesterosis. Zymosan was shown to consist of polysaccharides, proteins, fats, and inorganic elements; however, subsequent studies identified the active components of the yeast cell wall as a pure polysaccharide, specifically β-glucan. Repetition of biological assays with β-glucan indicated that most of the above functional activities identified with zymosan were retained by the purified β-glucan preparation.

The properties of β-glucan are quite similar to those of endotoxin in increasing nonspecific immunity and resistance to infection. The activities of β-glucan as an immune adjuvant and hemopoietic stimulator compare to those of more complex biological response modifiers (BRMs), such as bacillus Calmette-Guerin (BCG) and *Corynebacterium parvum*. The functional activities of yeast β-glucan are also comparable to those structurally similar carbohydrate polymers isolated from fungi and plants. These higher-molecular weight β-(1–3)-D-glucans such as schizophyllan, lentinan, krestin, grifolan, and pachyman exhibit similar immunomodulatory activities. A common mechanism shared by all these β-glucan preparations is their stimulation of cytokines such as interleukin-1 (IL-1) and tumor necrosis factor (TNF). Lentinan has been extensively investigated for its antitumor properties, both in animal models at 1 mg/kg for 10 days and in clinical trials since the late 1970s in Japan for advanced or recurrent malignant lymphoma and colorectal, mammary, lung and gastric cancers. In cancer chemotherapy, lentinan has been administered at 0.5–5 mg/day, I. M. or I. V., two or three times per week alone, or in combination with antineoplastic drugs. In addition to the activities ascribed to yeast glucans, studies suggest lentinan acts as a T-cell immunopotentiator, inducing cytotoxic activities, including production of IL-1, colony stimulating factor (CSF) and IL-3. (Chihara et al., 1989, *Int. J. Immunotherapy*, 4:145–154; Hamuro and Chihara, In *Lentinan, An Immunopotentiator*)

Various preparations of both particulate and soluble β-glucans have been tested in animal models to specify biological activities. The use of soluble and insoluble β-glucans alone or as vaccine adjuvants for viral and bacterial antigens has been shown in animal models to markedly increase resistance to a variety of bacterial, fungal, protozoan and viral infections. The hemopoietic effects of β-glucan have been related to increased peripheral blood leukocyte counts and bone marrow and splenic cellularity, reflecting increased numbers of granulocyte-macrophage progenitor cells, splenic pluripotent stem cells, and erythroid progenitor cells, as well as, increased serum levels of granulocyte-monocyte colony-stimulating factor (GM-CSF). Furthermore, the hemopoietic and anti-infective effects of β-glucan were active in cyclophosphamide-treated immunosuppressed animals. β-glucan was shown to be beneficial in animal models for trauma, wound healing and tumorigenesis. However, various insoluble and soluble preparations of β-glucan differed significantly in biological specificity and potency, with effective dosages varying from 25 to 500 mg/kg I. V. or I. P. in models for protection against infection and for hemopoiesis. Insoluble preparations demonstrated undesirable toxicological properties manifested by hepatosplenomegaly and granuloma formation. Clinical interest focused on a soluble glucan preparation which would retain biological activity yet yield negligible toxicity when adminsistered systemically. Chronic systemic administration of a soluble phosphorylated glucan over a wide range of doses (40–1000 mg/kg) yielded negligible toxicity in animals (DiLuzio et al., 1979, *Int. J. of Cancer*, 24:773–779; DiLuzio, U.S. Pat. No. 4,739,046).

The molecular mechanism of action of β-glucan has been elucidated by the demonstration of specific β-glucan receptor binding sites on the cell membranes of human neutrophils and macrophages. Mannans, galactans, $\alpha(1-4)$-linked glucose polymers and $\beta(1-4)$-linked glucose polymers have no avidity for this receptor. These β-glucan binding sites are opsonin-independent phagocytic receptors for particulate activators of the alternate complement pathway, similar to *Escherichia coli* lipopolysaccharide (LPS), inulin and some animal red blood cells. Ligand binding to the β-glucan receptor, in the absence of antibody, results in complement activation, phagocytosis, lysosomal enzyme release, and prostaglandin, thromboxane and leukotriene generation; thereby increasing nonspecific resistance to infection. However, all of the soluble β-glucan preparations described in the prior art demonstrated stimulation of cytokines.

Increases in plasma and splenic levels of interleukins 1 and 2 (IL-1, IL-2) in addition to tumor necrosis factor (TNF) were observed in vivo and corresponded to induction of synthesis of these cytokines in vitro. See Sherwood et al., 1987, *Int. J. Immunopharmac.*, 9:261–267 (enhancement of IL-1 and IL-2 levels in rats injected with soluble glucan); Williams et al., 1988, *Int. J. Immunopharmac.*, 10:405–414 (systemic administration of soluble glucan to AIDS patients increased IL-1 and IL-2 levels which were accompanied by chills and fever); Browder et al., 1990, *Ann. Surg.*, 211:605–613 (glucan administration to trauma patients increased serum IL-1 levels, but not TNF levels); Adachi et al., 1990, *Chem. Pharm. Bull.*, 38:988–992 (chemically cross-linked $\beta(1-3)$ glucans induce IL-1 production in mice).

Interleukin-1 (IL-1) is a primary immunologic mediator involved in cellular defense mechanisms. Numerous studies have been carried out on the application of IL-1 to enhance non-specific resistance to infection in a variety of clinical states. Pomposelli et al., *J. Parent. Ent. Nutr.*, 12(2):212–218, (1988). The major problem associated with the excessive stimulation or exogenous administration of IL-1 and other cellular mediators in humans is toxicity and side effects resulting from the disruption of the gentle balance of the immunoregulatory network. Fauci et al., *Annals. of Internal Medicine*, 106:421–433 (1987). IL-1 is an inflammatory cytokine that has been shown to adversely affect a variety of tissues and organs. For instance, recombinant IL-1 has been shown to cause death, hypotensive shock, leukopenia, thrombocytopenia, anemia and lactic acidosis. In addition, IL-1 induces sodium excretion, anorexia, slow wave sleep, bone resportion, decreased pain threshold and expression of many inflammatory-associated cytokines. It is also toxic to insulin secreting beta cells. Patients suffering from a number of inflammatory diseases already have elevated levels of IL-1 in their systems. Administration of agents that enhance further IL-1 production only exacerbate these inflammatory conditions. Thus, it would be beneficial to develop an agent that only selectively stimulates the immune system but which does not stimulate IL-1 or TNF.

Tumor necrosis factor (TNF) is also involved in infection, inflammation and cancer. Small amounts of TNF release growth factors while in larger amounts, TNF can cause septic shock, aches, pains, fever, clot blood, degrade bone and stimulate white blood cells and other immune defenses. Development of a drug which minimizes these adverse side affects caused by the release of TNF would be highly desirable, especially for individuals whose immune system has been activated due to infection, autoimmune disease or cancer.

SUMMARY OF THE INVENTION

The present invention relates to methods for stimulating platelet proliferation. The methods involve the administration of neutral soluble glucan preparations to a mammal in amounts sufficient to stimulate platelet proliferation. Neutral soluble glucan preparations useful for platelet stimulation have been described in U.S. Ser. Nos. 07/934,015, filed Aug. 21, 1992, and 07/855,578, filed Mar. 23, 1992, now issued as U.S. Pat. No. 5,488,040 the disclosures of which are incorporated herein by reference.

Neutral soluble β-glucans of the type described in U.S. Ser. No. 07/934,015, exert potent and specific immunological effects without stimulating the production of certain cytokines, preparations containing the neutral soluble β-glucans and a novel manufacturing process therefor are described. In the present method, soluble glucan which induces cytokine production is processed through a unique series of acid, alkaline and neutral treatments to yield a conformationally pure neutral soluble glucan preparation with unique biological properties. The neutral soluble glucan preparation retains a specific subset of immunological properties common to β-glucans but uniquely does not induce the production of IL-1 and TNF in vitro or in vivo.

The neutral soluble glucan preparation is produced by treating insoluble glucan with acid to produce a water soluble glucan, dissociating the native conformations of the soluble glucan at alkaline pH, purifying the desired molecular weight fraction at alkaline pH, re-annealing the dissociated glucan fraction under controlled conditions of time, temperature and pH to form a unique triple helical conformation, and further purifying under neutral pH to remove single helix and aggregated materials to yield a conformationally pure, neutral, water soluble, underivatized glucan which has a unique biological profile.

The neutral soluble glucan preparation has a high affinity for the β-glucan receptor of human monocytes and retains two primary biological activities, (1) the enhancement of microbicidal activity of phagocytic cells, and (2) monocyte and neutrophil hemopoietic activity. Unlike soluble glucans described in the prior art, the neutral soluble glucan of this invention neither induces nor primes IL-1 and TNF production in vitro and in vivo.

The neutral soluble glucan preparation is appropriate for parenteral (e.g., intravenous, intraperitoneal, subcutaneous, intramuscular), topical, oral or intranasal administration to humans and animals as an anti-infective to combat infection associated with burns, surgery, chemotherapy, bone marrow disorders and other conditions in which the immune system may be compromised. Neutral soluble glucan produced by the present method can be maintained in a clear solution and equilibrated in a pharmaceutically acceptable carrier. Safe and efficacious preparations of the neutral soluble glucan of the present invention can be used in therapeutic and/or prophylactic treatment regimens of humans and animals to enhance their immune response, without stimulating the production of certain biochemical mediators (e.g., IL-1, TNF and leukotrienes) that can cause detrimental side effects, such as fever and inflammation.

DETAILED DESCRIPTION OF INVENTION

The invention is directed toward the discovery of a neutral soluble β-glucan polymer that can bind to the β-glucan receptor and activate only a desired subset of immune responses. The terms "neutral soluble β-glucan" and "neutral soluble glucan" are intended to mean an aqueous soluble β-glucan having a unique triple helical conformation that results from the denaturation and re-annealing of aqueous soluble glucan.

This neutral soluble β-glucan has been shown to increase the number of neutrophils and monocytes as well as their direct infection fighting activity (phagocytosis and microbial killing). However, the neutral soluble β-glucan does not stimulate the production of biochemical mediators, such as IL-1, TNF and leukotrienes, that can cause detrimental side effects such as high fever, inflammation, wasting disease and organ failure. These advantageous properties make neutral soluble glucan preparations of this invention useful in the prevention and treatment of infection because they selectively activate only those components of the immune system responsible for the initial response to infection, without stimulating the release of certain biochemical mediators that can cause adverse side effects. The solution containing the neutral soluble β-glucan also lacks the toxicity common to many immunomodulators.

Figure 1:
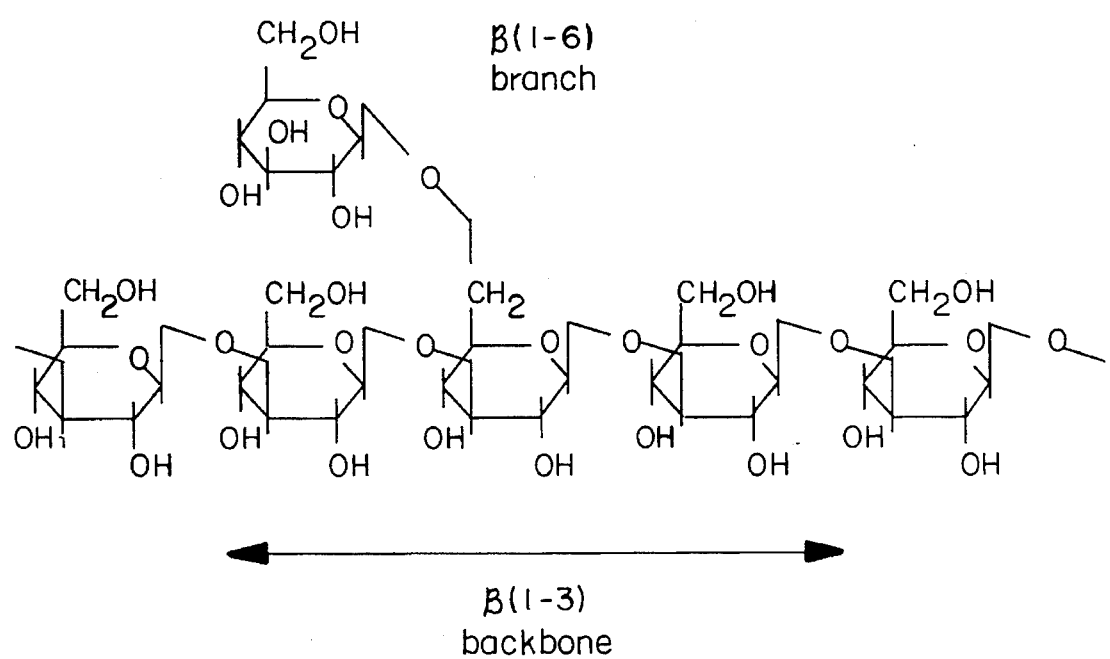
FIG. 1 shows the general structure of neutral soluble glucan as being a linear β(1–3)-linked glucose polymer having periodic branching via a single β(1–6)-linked glucose moiety.

The neutral soluble β-glucans of this invention are composed of glucose monomers organized as a β(1–3) linked glucopyranose backbone with periodic branching via β(1–6) glycosidic linkages. The neutral soluble glucan preparations contain glucans, which have not been substantially modified by substitution with functional (e.g., charged) groups or other covalent attachments. The general structure of the neutral soluble glucan is shown in FIG. 1. The biologically active preparation of this invention is a conformationally purified form of β-glucan produced by dissociating the native glucan conformations and re-annealing and purifying the resulting unique triple helical conformation. The unique conformation of the neutral soluble glucan contributes to the glucan's ability to selectively activate the immune system without stimulating the production of detrimental biochemical mediators.

The neutral soluble glucan preparations of this invention are prepared from insoluble glucan particles, preferably derived from yeast organisms. See Manners et al., *Biochem. J.*, 135:19–30, (1973) for a general procedure to make insoluble yeast glucans. Glucan particles which are particularly useful as starting materials in the present invention are whole glucan particles (WGP) described by Jamas et al., in U.S. Pat. Nos. 4,810,646, 4,992,540, 5,082,936 and 5,028,703, the teachings of all of which are hereby incorporated herein by reference. The source of the whole glucan particles can be the broad spectrum of glucan-containing fungal organisms which contain β-glucans in their cell walls. Whole glucan particles obtained from the strains *Saccharomyces cerevisiae* R4 (NRRL Y-15903; deposit made in connection with U.S. Pat. No. 4,810,646) and R4 Ad (ATCC No. 741/81.) are particularly useful. Other strains of yeast that can be used include *Saccharomyces delbrueckii, Saccharomyces rosei, Saccharomyces microellipsodes, Saccharomyces carlsbergensis, Schizosaccharomyces pombe, Kluyveromyces lactis, Kluyveromyces fragilis, Kluyveromyces polysporus, Candida albicans, Candida cloacae, Candida tropicalis, Candida utilis, Hansenula wingei, Hansenula arni, Hansenula henricii, Hansenula americana*.

A procedure for extraction of whole glucan particles is described by Jamas et al., in U.S. Pat. Nos. 4,810,646, 4,992,540, 5,082,936 and 5,028,703. For the purpose of this present invention it is not necessary to conduct the final organic extraction and wash steps described by Jamas et al.

In the present process, whole glucan particles are suspended in an acid solution under conditions sufficient to dissolve the acid-soluble glucan portion. For most glucans, an acid solution having a pH of from about 1 to about 5 and at a temperature of from about 20 to about 100° C. is sufficient. Preferably, the acid used is an organic acid capable of dissolving the acid-soluble glucan portion. Acetic acid, at concentrations of from about 0.1 to about 5M or formic acid at concentrations of from about 50% to 98% (w/v) are useful for this purpose. The treatment time may vary from about 10 minutes to about 20 hours depending on the acid concentration, temperature and source of whole glucan particles. For example, modified glucans having more β(1–6) branching than naturally-occurring, or wild-type glucans, require more stringent conditions, i.e., longer exposure times and higher temperatures. This acid-treatment step can be repeated under similar or variable conditions. One preferred processing method is described in the exemplification using glucan derived from *S. cerevisiae* strain R4 Ad. In another embodiment of the present method, whole glucan particles from the strain, *S. cerevisiae* R4, which have a higher level of β(1–6) branching than naturally-occurring glucans, are used, and treatment is carried out with 90% (by wt.) formic acid at 20° C. for about 20 minutes and then at 85° C. for about 30 minutes.

The insoluble glucan particles are then separated from the solution by an appropriate separation technique, for example, by centrifugation or filtration. The pH of the resulting slurry is adjusted with an alkaline compound such as sodium hydroxide, to a pH of about 7 to about 14. The precipitate is collected by centrifugation and is boiled in purified water (e.g., USP) for three hours. The slurry is then resuspended in hot alkali having a concentration sufficient to solubilize the glucan polymers. Alkaline compounds which can be used in this step include alkali-metal or alkali-earth metal hydroxides, such as sodium hydroxide or potassium hydroxide, having a concentration of from about 0.01 to about 10N. This step can be conducted at a temperature of from about 4° C. to about 121° C., preferably from about 20° C. to about 100° C. In one embodiment of the process, the conditions utilized are a 1M solution of sodium hydroxide at a temperature of about 80°–100° C. and a contact time of approximately 1–2 hours. The resulting mixture contains solubilized glucan molecules and particulate glucan residue and generally has a dark brown color due to oxidation of contaminating proteins and sugars. The particulate residue is removed from the mixture by an appropriate separation technique, e.g., centrifugation and/or filtration. In another embodiment of the process the acid-soluble glucans are precipitated after the preceding acid hydrolysis reaction by the addition of about 1.5 volumes of ethanol. The mixture is chilled to about 4° C. for two (2) hours and the resulting precipitate is collected by centrifugation or filtration and washed with water. The pellet is then resuspended in water, and stirred for three (3) to twelve (12) hours at a temperature between about 20° C. and 100° C. At this point the pH is adjusted to approximately 10 to 13 with a base such as sodium hydroxide.

The resulting solution contains dissociated soluble glucan molecules. This solution is now purified to remove traces of insoluble glucan and high molecular weight soluble glucans which can cause aggregation. This step can be carried out by an appropriate purification technique, for example, by ultrafiltration, utilizing membranes with nominal molecular weight levels (NMWL) or cut-offs in the range of about 1,000 to 100,000 daltons. It was discovered that in order to prevent gradual aggregation or precipitation of the glucan polymers the preferred membrane for this step has a nominal molecular weight cut-off of about 100,000 daltons. The soluble glucan is then further purified at alkaline pH to remove low molecular weight materials. This step can be carried out by an appropriate purification technique, for example, by ultrafiltration, utilizing membranes with nominal molecular weight/levels or cut-offs in the range of 1,000 to 30,000 daltons.

The resulting dissociated soluble glucan is re-annealed under controlled conditions of time (e.g., from about 10 to about 120 minutes), temperature (e.g., from about 50° to about 70° C.) and pH. The pH of the solution is adjusted in the range of about 6–8 with an acid, such as hydrochloric acid. The purpose of this re-annealing step is to cause the soluble glucan to rearrange from a single helix conformation to a new ordered triple helical conformation. The re-annealed glucan solution is then size fractionated using 30,000–100,000 NMW and 150,000–500,000 NMW cut-off membrane ultrafilters to selectively remove high and low molecular weight soluble glucans. Prior to sizing, the soluble glucans exist as a mixture of conformations including random coils, gel matrices or aggregates, triple helices and single helices. The objective of the sizing step is to obtain an enriched fraction for the re-annealed conformation of specific molecular weight. The order in which the ultrafilters are used is a matter of investigator preference and should result in the same desired product.

The concentrated fraction obtained after this step is enriched in the soluble, biologically active neutral soluble glucan. The glucan concentrate is further purified, for example, by diafiltration using a 10,000 dalton membrane. The preferred concentration of the soluble glucan after this step is from about 2 to about 10 mg/ml.

The neutralized solution is then further purified, for example, by diafiltration, using a pharmaceutically acceptable medium (e.g., sterile water for injection, phosphate-buffered saline (PBS), isotonic saline, dextrose) suitable for parenteral administration. The preferred membrane for this diafiltration step has a nominal molecular weight cut-off of about 10,000 daltons. The final concentration of the glucan solution is adjusted in the range of about 0.5 to 10 mg/ml. In accordance with pharmaceutical manufacturing standards for parenteral products, the solution can be terminally sterilized by filtration through a 0.22 μm filter. The neutral soluble glucan preparation obtained by this process is sterile, non-antigenic, and essentially pyrogen-free, and can be stored at room temperature (e.g., 15°–30° C.) for extended periods of time without degradation. This process is unique in that it results in a neutral aqueous solution of (pH 4.5 to 7.0) immunologically active glucans which is suitable for parenteral administration.

For purposes of the present invention, the term "soluble" as used herein to describe glucans obtained by the present process, means a visually clear solution can be formed in an aqueous medium such as water, PBS, isotonic saline, or a dextrose solution having a neutral pH (e.g., from about ph 5 to about 7.5), at room temperature (about 20°–25° C.) and at a concentration of up to about 10 mg/ml. The term "aqueous medium" refers to water and water-rich phases, particularly to pharmaceutically acceptable aqueous liquids, including PBS, saline and dextrose solutions.

The resulting solution is substantially free of protein contamination, is non-antigenic, non-pyrogenic and is pharmaceutically acceptable for parenteral administration to animals and humans. However, if desired, the soluble glucan can be dried by an appropriate drying method, such as lyophilization, and stored in dry form.

The neutral soluble glucans of this invention can be used as safe, effective, therapeutic and/or prophylactic agents, either alone or as adjuvants, to enhance the immune response in humans and animals. Soluble glucans produced by the present method selectively activate only those components that are responsible for the initial response to infection, without stimulating or priming the immune system to release certain biochemical mediators (e.g., IL-1, TNF, IL-6, IL-8 and GM-CSF) that can cause adverse side effects. As such, the present soluble glucan composition can be used to prevent or treat infectious diseases in malnourished patients, patients undergoing surgery and bone marrow transplants, patients undergoing chemotherapy or radiotherapy, neutropenic patients, HIV-infected patients, trauma patients, burn patients, patients with chronic or resistant infections such as those resulting from myelodysplastic syndrome, and the elderly, all of who may have weakened immune systems. An immunocompromised individual is generally defined as a person who exhibits an attenuated or reduced ability to mount a normal cellular or humoral defense to challenge by infectious agents, e.g., viruses, bacteria, fungi and protozoa. A protein malnourished individual is generally defined as a person who has a serum albumin level of less than about 3.2 grams per deciliter (g/dl) and/or unintentional weight loss of greater than 10% of usual body weight.

More particularly, the method of the invention can be used to therapeutically or prophylactically treat animals or humans who are at a heightened risk of infection due to imminent surgery, injury, illness, radiation or chemotherapy, or other condition which deleteriously affects the immune system. The method is useful to treat patients who have a disease or disorder which causes the normal metabolic immune response to be reduced or depressed, such as HIV infection (AIDS). For example, the method can be used to pre-initiate the metabolic immune response in patients who are undergoing chemotherapy or radiation therapy, or who are at a heightened risk for developing secondary infections or post-operative complications because of a disease, disorder or treatment resulting in a reduced ability to mobilize the body's normal metabolic responses to infection. Treatment with the neutral soluble glucans has been shown to be particularly effective in mobilizing the host's normal immune defenses, thereby engendering a measure of protection from infection in the treated host.

The present composition is generally administered to an animal or a human in an amount sufficient to produce immune system enhancement. The mode of administration of the neutral soluble glucan can be oral, enteral, parenteral, intravenous, subcutaneous, intraperitoneal, intramuscular, topical or intranasal. The form in which the composition will be administered (e.g., powder, tablet, capsule, solution, emulsion) will depend on the route by which it is administered. The quantity of the composition to be administered will be determined on an individual basis, and will be based at least in part on consideration of the severity of infection or injury in the patient, the patient's condition or overall health, the patient's weight and the time available before surgery, chemotherapy or other high-risk treatment. In general, a single dose will preferably contain approximately 0.01 to approximately 10 mg of modified glucan per kilogram of body weight, and preferably from about 0.1 to 2.5 mg/kg. The dosage for topical application will depend upon the particular wound to be treated, the degree of infection and severity of the wound. A typical dosage for wounds will be from about 0.001 mg/ml to about 2 mg/ml, and preferably from about 0.01 to about 0.5 mg/ml.

In general, the compositions of the present invention can be administered to an individual periodically as necessary to stimulate the individual's immune response. An individual skilled in the medical arts will be able to determine the length of time during which the composition is administered and the dosage, depending on the physical condition of the patient and the disease or disorder being treated. As stated above, the composition may also be used as a preventative treatment to pre-initiate the normal metabolic defenses which the body mobilizes against infections.

Neutral soluble β-glucan can be used for the prevention and treatment of infections caused by a broad spectrum of bacterial, fungal, vital and protozoan pathogens. The prophylactic administration of neutral soluble β-glucan to a person undergoing surgery, either preoperatively, intraoperatively and/or post-operatively, will reduce the incidence and severity of post-operative infections in both normal and high-risk patients. For example, in patients undergoing surgical procedures that are classified as contaminated or potentially contaminated (e.g., gastrointestinal surgery, hysterectomy, cesarean section, transurethral prostatectomy) and in patients in whom infection at the operative site would present a serious risk (e.g., prosthetic arthroplasty, cardiovascular surgery), concurrent initial therapy with an appropriate antibacterial agent and the present neutral soluble glucan preparation will reduce the incidence and severity of infectious complications.

In patients who are immunosuppressed, not only by disease (e.g., cancer, AIDS) but by courses of chemotherapy and/or radiotherapy, the prophylactic administration of the soluble glucan will reduce the incidence of infections caused by a broad spectrum of opportunistic pathogens including many unusual bacteria, fungi and viruses. Therapy using neutral soluble β-glucan has demonstrated a significant radio-protective effect with its ability to enhance and prolong macrophage function and regeneration and, as a result enhance resistance to microbial invasion and infection.

In high risk patients (e.g., over age 65, diabetics, patients having cancer, malnutrition, renal disease, emphysema, dehydration, restricted mobility, etc.) hospitalization frequently is associated with a high incidence of serious nosocomial infection. Treatment with neutral soluble β-glucan may be started empirically before catheterization, use of respirators, drainage tubes, intensive care units, prolonged hospitalizations, etc. to help prevent the infections that are commonly associated with these procedures. Concurrent therapy with antimicrobial agents and the neutral soluble β-glucan is indicated for the treatment of chronic, severe, refractory, complex and difficult to treat infections.

The compositions administered in the method of the present invention can optionally include other components, in addition to the neutral soluble β-glucan. The other components that can be included in a particular composition are determined primarily by the manner in which the composition is to be administered. For example, a composition to be administered orally in tablet form can include, in addition to neutral soluble β-glucan, a filler (e.g., lactose), a binder (e.g., carboxymethyl cellulose, gum arabic, gelatin), an adjuvant, a flavoring agent, a coloring agent and a coating material (e.g., wax or plasticizer). A composition to be administered in liquid form can include neutral soluble β-glucan and, optionally, an emulsifying agent, a flavoring agent and/or a coloring agent. A composition for parenteral administration can be mixed, dissolved or emulsified in water, sterile saline, phosphate buffered saline (PBS), dextrose or other biologically acceptable carrier. A composition for topical administration can be formulated into a gel, ointment, lotion, cream or other form in which the composition is capable of coating the site to be treated, e.g., wound site.

Compositions comprising neutral soluble glucan can also be administered topically to a wound site to stimulate and enhance wound healing and repair. Wounds due to ulcers, acne, vital infections, fungal infections or periodontal disease, among others, can be treated according to the methods of this invention to accelerate the healing process. Alternatively, the neutral soluble β-glucan can be injected into the wound or afflicted area. In addition to wound repair, the composition can be used to treat infection associated therewith or the causative agents that result in the wound. A composition for topical administration can be formulated into a gel, ointment, lotion, cream or other form in which the composition is capable of coating the site to be treated, e.g., wound site. The dosage for topical application will depend upon the particular wound to be treated, the degree of infection and severity of the wound. A typical dosage for wounds will be from about 0.01 mg/ml to about 2 mg/ml, and preferably from about 0.01 to about 0.5 mg/ml.

Another particular use of the compositions of this invention is for the treatment of myelodysplastic syndrome (MDS). MDS, frequently referred to as preleukemia syndrome, is a group of clonal hematopoietic stem cell disorders characterized by abnormal bone marrow differentiation and maturation leading to peripheral cytopenia with high probability of eventual leukemic conversion. Recurrent infection, hemorrhaging and terminal infection resulting in death typically accompany MDS. Thus, in order to reduce the severity of the disease and the frequency of infection, compositions comprising modified glucan can be chronically administered to a patient diagnosed as having MDS according to the methods of this invention, in order to specifically increase the infection fighting activity of the patient's white blood cells. Other bone marrow disorders, such as aplastic anemia (a condition of quantitatively reduced and defective hematopoiesis) can be treated to reduce infection and hemorrhage that are associated with this disease state.

Neutral soluble glucan produced by the present method enhances the non-specific defenses of mammalian mononuclear cells and significantly increases their ability to respond to an infectious challenge. The unique property of neutral soluble glucan macrophage activation is that it does not result in increased body temperature (i.e., fever) as has been reported with many non-specific stimulants of those defenses. This critical advantage of neutral soluble glucan may lie in the natural profile of responses it mediates in white blood cells. It has been shown that the neutral soluble β-glucan of the present invention selectively activates immune responses but does not directly stimulate or prime cytokine (e.g., IL-1 and TNF) release from mononuclear cells, thus distinguishing the present neutral soluble glucan from other glucan preparations (e.g., lentinan, krestin) and immunostimulants.

In addition, it has been demonstrated herein that the neutral soluble glucan preparation of the present invention possesses an unexpected platelet stimulating property. Although it was known that glucans have the ability to stimulate white blood cell hematopolesis, the disclosed platelet stimulating property had not been reported or anticipated. This property can be exploited in a therapeutic regimen for use as an adjuvant in parallel with radiation or chemotherapy treatment. Radiation and chemotherapy are known to result in neutropenia (reduced polymorphonuclear (PMN) leukocyte cell count) and thrombocytopenia (reduced platelet count). At present, these conditions are treated by the administration of colony-stimulating factors such as GM-CSF and G-CSF. Such factors are effective in overcoming neutropenia, but fail to impact upon thrombocytopenia. Thus, the platelet stimulating property of the neutral soluble glucan preparation of this invention can be used, for example, as a therapeutic agent to prevent or minimize the development of thrombocytopenia which limits the dose of the radiation or chemotherapeutic agent which is used to treat cancer.

The invention is further illustrated by the following Examples.

EXAMPLES

Example 1

Preparation of Neutral Soluble Glucan from *S. cerevisiae*

*Saccharomyces cerevisiae* strain R4 Ad (a non-recombinant derivative of wild-type strain A364A), was grown in a large-scale fermentation culture using a defined glucose, ammonium sulfate minimal medium. The production culture was maintained under glucose limitation in a feed-batch mode (New Brunswick MPP80). When the growing culture reached late logarithmic phase, the fermentation was ended and the poly-(1–6)-β-D-glucopyranosyl-(1–3)-β-D-glucopyranose (PGG) was stabilized by adjusting the culture to pH 12±0.5 using 10M NaOH. The yeast cells containing PGG were harvested by continuous-flow centrifugation (Westfalia SA-1). After centrifugation, the cells were collected into a stainless steel extraction vessel.

The first step in the extraction process was an alkaline extraction accomplished by mixing the cells with 1M sodium hydroxide (NaOH) at 90°±5° C. for 1 hour. Upon completion of this alkaline extraction, the β-glucan remained in the solid phase, which was collected by continuous centrifugation (Westfalia SA-1). The collected cell wall fraction was extracted a second time using the same procedure and under the same conditions. Treatment with alkali hydrolyzed and solubilized the cellular proteins, nucleic acids, mannans, soluble glucans and polar lipids into the supernatant fraction, and deacetylated chitin to chitosan in the cell wall.

The second step in the extraction process was a pH 4.5±0.05 (adjusted with concentrated HCl) extraction at 75°± 5° C. for 1 hour. This was followed by a 0.1M acetic acid extraction to complete the removal of glycogen, chitin, chitosan and remaining proteins. The solids were collected and rinsed twice with Purified Water USP to remove any residual acid as well as any yeast degradation products.

The third step in the extraction process was a set of six organic extractions. The first four extractions were carried out in isopropanol. The solids were collected by centrifugation and then subjected to two acetone extractions. The two-stage organic extractions eliminated nonpolar lipids and hydrophobic proteins which may have co-purified with the drug substance. The resulting wet solids were dried in a vacuum oven at 65°±5° C. for 48–96 hours to yield a free-flowing powder.

At this stage the extraction process yielded a stable, insoluble intermediate consisting of approximately 90% β-glucan, called whole glucan particles (WGPs). The dry WGP intermediate was stored at 15°–30° C. until further use.

The WGP powder was resuspended in 98% formic acid, in a glass reaction vessel at room temperature. The resulting mixture was heated to 85°±5° C. for 20 minutes. Under these conditions, the WGPs were partially hydrolyzed and solubilized to provide the desired molecular weight distribution of soluble PGG which was then precipitated by adding 1.5 volumes of ethanol. After complete mixing, the preparation was centrifuged to collect the β-glucan precipitate. Any residual formic acid was removed by boiling the β-glucan preparation in Purified Water USP for three hours.

Any unhydrolyzed WGPs were then removed from the β-glucan solution by centrifugation. The β-glucan solution was raised to pH 12.5±0.5 by the addition of the concentrated sodium hydroxide. The remaining purification steps were carried out by ultrafiltration.

The soluble alkaline β-glucan preparation was passed through a 100,000 nominal molecular weight cut-off (NMW) membrane ultra filter (Amicon DC10). Under alkaline conditions this membrane ultrafilter removed insoluble and high molecular weight soluble β-glucan. Trace low molecular weight degradation products were then removed by recirculation through a 10,000 NMW cut-off membrane ultrafilter. The ultrafiltration was conducted as a constant volume wash with 0.1M NaOH.

The β-glucan solution was re-annealed under controlled conditions by adjusting to pH 7.0±0.5 with concentrated hydrochloric acid, heating to 60°±10° C., held for 20 minutes and cooled. The neutral re-annealed solution was then concentrated and washed with Sodium Chloride Injection USP in a 70,000 NMW cut-off membrane ultrafilter (Filtron Minisep) to enrich for the re-annealed neutral soluble glucans. Next the material was filtered through a 300,000 NMW cut-off membrane ultrafilter (Filtron Minisep) to remove high molecular weight and aggregated glucan molecules. In the same ultrafilter, the neutral soluble glucan material was washed with Sodium Chloride Injection USP in a constant volume wash mode.

The neutral soluble glucan was then concentrated in a 10,000 NMW cut-off membrane ultrafilter. The concentration process continued until a concentration of at least 1.0 mg/ml hexose equivalent was achieved.

The resulting neutral soluble glucan was then subjected to filtration through a depyrogenating filter (0.1 micron Posidyne) and a sterile 0.2 micron filter (Millipak) to yield sterile, pyrogen-free neutral soluble glucan. The neutral soluble glucan solution was stored at controlled room temperature (15°–30° C.) until further use. The aqueous solubility of neutral soluble glucan in the pH range of 4 to 8 is approximately 100 mg/ml. The solubility increased with increasing pH and reached approximately, 150 mg/ml at pH 13.

Example 2

ANALYSIS OF NEUTRAL SOLUBLE GLUCAN

A. Glucose, Mannose and Glucosamine.

Monosaccharide analysis was performed to quantitate the relative amounts of β-glucan (as glucose), mannan or phosphomannan (as mannose), and chitin (as N-acetyl glucosamine) in the neutral soluble glucan. The sample was hydrolyzed to monosaccharides in 2M trifluoroacetic acid for 4 h at 110° C., evaporated to dryness, and redissolved in water. Monosaccharides were separated on a Dionex HPLC system using a CarboPac PA100 column (4×250 mm) using 5M NaOH at 1 ml/min. and quantitated using a pulsed electro-chemical detector (Dionex Model PED-1). The sensitivity of this assay for monosaccharides is 0.1% (w/w).

Glucose (retention time of 16.6 min) was identified as the only monosaccharide component of neutral soluble glucan along with traces of glucose degradation products (from hydrolysis) anhydroglucose at 2.5 min. and 5-hydroxymethyl-furfural at 4.3 min. The results confirm that neutral soluble glucan consisted of ≧98% glucose.

B. FTIR

Fourier transform infrared spectroscopy by diffuse reflectance (FTIR, Matson Instruments, Polaris) of lyophilized neutral soluble glucan samples was used to determine the anomeric structure (α vs. β), and linkage type (β(1–3), β(1–6), β(1–4)) present in neutral soluble glucan. Absorption maxima of 890 cm$^{-1}$ identified β(1–3) linkages; 920 cm$^{-1}$ identified β(1–6) linkages. No presence of α-linked anomers (850 cm$^{-1}$) (e.g., glycogen) or β(1–4)-linked polysaccharides (e.g., chitin, 930 cm$^{-1}$) were detected.

Example 3

CONFORMATIONAL ANALYSIS

Figure 2:
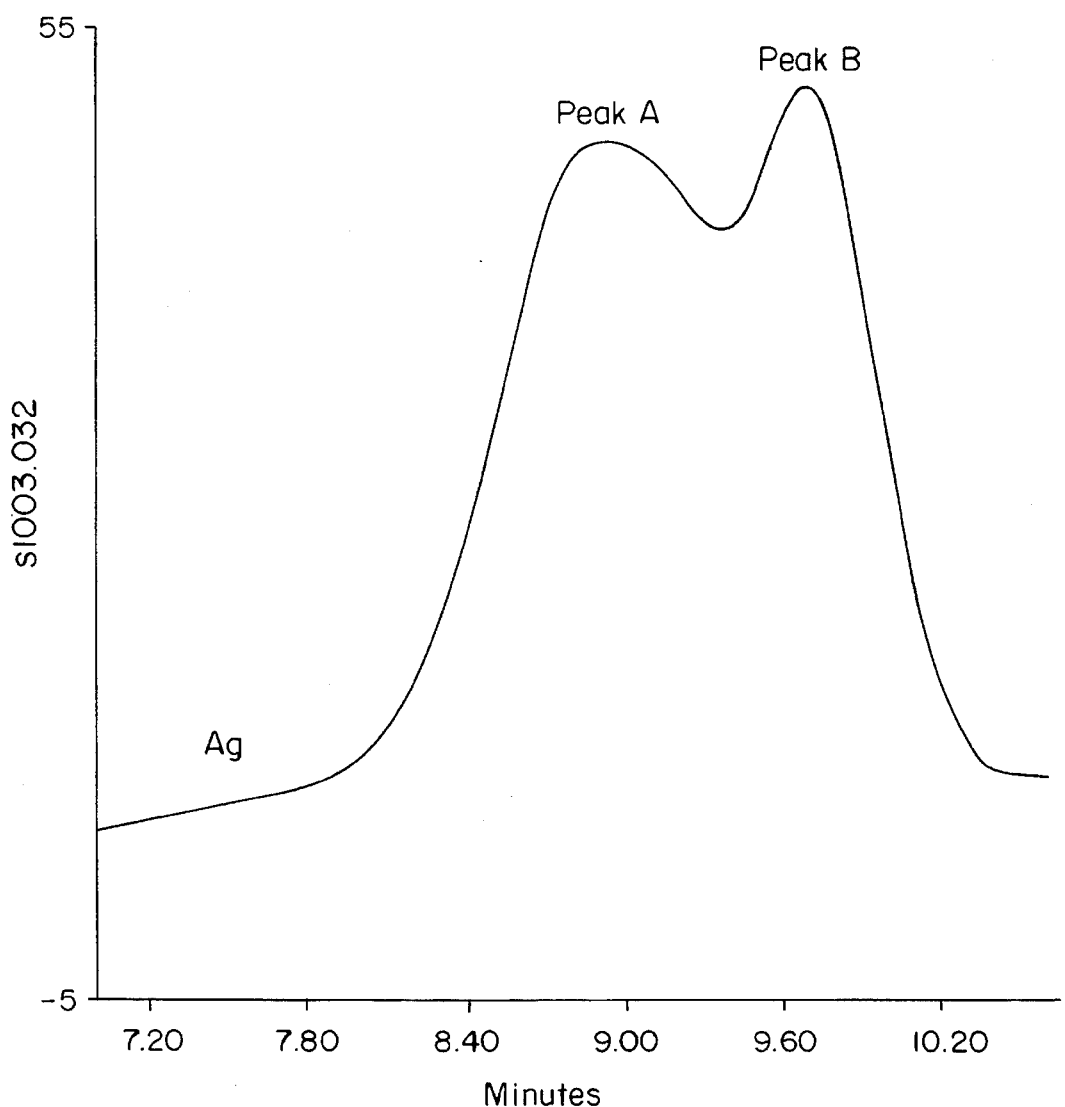
FIG. 2 shows a gel permeation chromatogram (pH 7) of soluble glucan which has not been purified by alkali dissociation and re-annealing. The chromatogram shows three species, referred to herein as high molecular weight aggregate (Ag), Peak A (triple helix glucan) and Peak B (single helix glucan).
Figure 3:
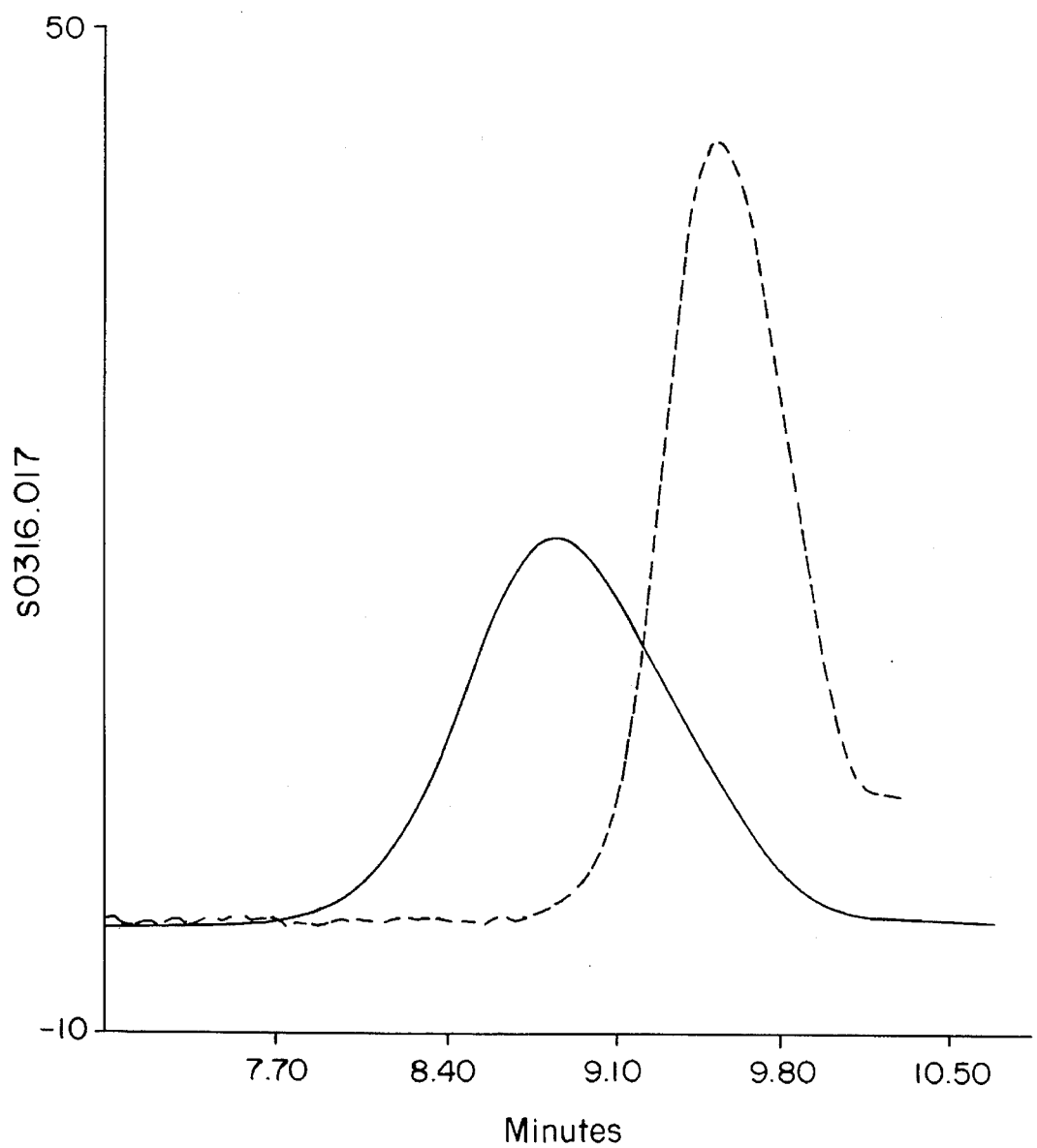
FIG. 3 is a chromatogram obtained for the neutral soluble glucan by gel permeation chromatography. The solid line represents the neutral soluble glucan at ph 7 and the broken line represents the neutral soluble glucan at ph 13.
Figure 4:
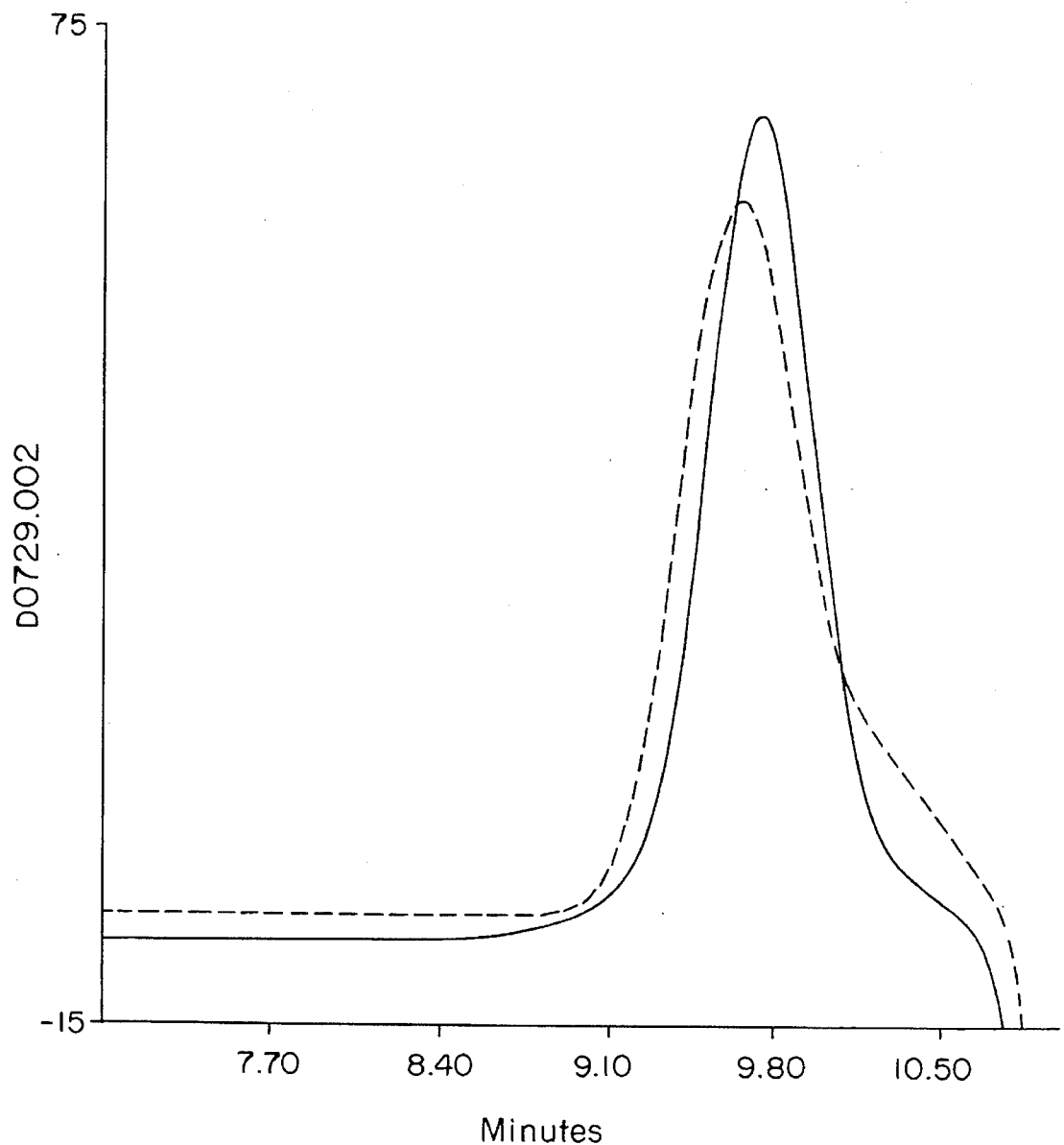
FIG. 4 is a chromatogram obtained for the single helix β-glucan (Peak B) by gel permeation chromatography. The solid line represents Peak B at ph 7 and the broken line represents Peak B at ph 13.

A solution of β-glucan which was not processed by alkali dissociation and re-annealing was analyzed for its compositional identity by gel permeation chromatography (pH 7) and found to contain multiple species, referred to herein as high molecular weight aggregate (Ag), Peak A and Peak B (See FIG. 2). Neutral soluble glucan which was prepared by alkali dissociation and re-annealing as described in Example 1, is present as a single peak (see FIG. 3) with an average molecular weight of 92,660 daltons at pH 7. The distinct conformations of neutral soluble glucan and Peak B were demonstrated by gel permeation chromatography (GPC) at pH 7 and pH 13 using a refractive index detector. Neutral soluble glucan underwent a significant conformational transition from pH 7 to pH 13 which illustrates complete dissociation of the multiple helix at pH 7 to a single helical form at pH 13 (see FIG. 3). In contrast, Peak B only underwent a slight shift in molecular weight from pH 7 to pH 13 (see FIG. 4). The molecular weight of neutral soluble glucan and Peak B glucans as a function of pH is shown below in Table 1.

TABLE 1

| Sample | Mw pH 7 | Mw pH 13 | Mw Ratio (pH 7/pH 13) |
| --- | --- | --- | --- |
| Neutral soluble glucan | 92,666 | 18,693 | 4.96 |
| Peak B | 8,317 | 7,168 | 1.16 |

The conformation of neutral soluble glucan and Peak B glucan was also determined by aniline blue complexing (Evans et al., 1984, *Carb. Pol.*, 4:215–230; Adachi et al., 1988, *Carb. Res.*, 177:91–100), using curdlan, a linear β(1–3) glucan, as the triple helix control and pustulan, a β(1–6) glucan, as a non-ordered conformational control. The results are discussed below and shown in Table 2.

The curdlan triple helix control complexed with aniline blue resulting in high fluorescence. Increasing the NaOH concentration began to dissociate the curdlan triple helix slightly, but NaOH concentrations >0.25M are required for complete dissociation of curdlan. The pustulan non-ordered control only formed a weak complex with aniline blue resulting in low fluorescence measurements which were not affected by NaOH concentration.

The neutral soluble glucan complexed effectively with aniline blue at low NaOH concentration (25 mM NaOH) resulting in high fluorescence. However, the neutral soluble glucan conformation dissociated significantly (50%) at NaOH concentrations as low as 150 mM NaOH indicating that it exists as a unique conformation compared to naturally occurring β-glucans, such as laminarin and curdlan, which require significantly higher NaOH concentrations for dissociation to occur. Peak B formed a weak complex with aniline blue due to its single helical conformation.

TABLE 2

Conformational Analysis of Glucans by Aniline Blue Complexing

| Test Material | Fluorescence | | |
| --- | --- | --- | --- |
| | 25 mM NaOH | 100 mM NaOH | 150 mM NaOH |
| Blank | 0 | 2 | 0 |
| Curdlan β(1–3) glucan | 53.5 | 41.6 | 36 |
| Pustulan β(1–6) glucan | 9.8 | 8.3 | 8.0 |
| Neutral soluble glucan | 40 | 25.6 | 20.2 |
| Peak B | 12.4 | 6.2 | 4.1 |

Example 4

EFFECTS OF NEUTRAL SOLUBLE GLUCAN ON HUMAN MONOCYTE PRODUCTION OF TNFα

Human peripheral blood mononuclear cells were isolated (Janusz et al., (1987), *J. Immunol.*, 138: 3897–3901) from normal citrated and dextran-treated blood, washed in Hank's balanced salts solution (HBSS), lacking calcium, magnesium, and phenol red, and purified by gradient centrifugation on cushions of Ficoll-Paque (Pharmacia Fine Chemicals, Piscataway, N.J.). The mononuclear cells were collected into HBSS, washed twice, resuspended in RPMI 1640 Medium (Gibco, Grand Island, N.Y.) containing 1% heat-inactivated autologous serum (56° C. for 30 min.), and counted on the Coulter counter.

For the preparation of monocyte monolayers, 1 ml of $2.2 \times 10^6$ mononuclear cells/ml was plated into wells of 24-well tissue culture plates (CoStar, Cambridge, Mass.), incubated for 1 h at 37° C. in a humidified atmosphere of 5% $CO_2$, and washed three times with RPMI to remove nonadherent cells. A second 1 ml aliquot of $2.2 \times 10^6$ mononuclear cells/ml was layered into each well and incubated for 2 hours as described above before removal of the nonadherent cells. By visual enumeration at 40× with an inverted phase microscope and a calibrated reticule, the number of adherent cells for 30 different donors was $0.77 \pm 0.20 \times 10^6$ per well (mean±SD). By morphology and nonspecific esterase staining, >95% of the adherent cells were monocytes.

Monocyte monolayers were incubated at 37° C. in the $CO_2$ chamber for 0 to 8 h with 0.5 ml of RPMI, 1% heat-inactivated autologous serum, 10 mM HEPES, and 5 mM $MgCl_2$ in the absence and presence of various glucan preparations. The culture supernatant was removed, clarified by centrifugation at 14,000 g for 5 min at 4° C., and stored at −70° C. before assay of cytokines.

The concentration of TNF-α in the monocyte supernatants was measured by an enzyme-linked immunosorbent assay (ELISA) with the BIOKINE TNF Test kit (T Cell Sciences, Cambridge, Mass.), which had a lower limit of detectability of 40 pg/ml. The data are expressed as pg per $10^6$ monocytes, which was calculated by dividing the quantity of cytokine in 0.5 ml of supernatant by the number of monocytes per well.

For the determination of cell-associated levels of TNF-α, the adherent monocytes were lysed in 0.25 ml PBS by three rounds of freezing and thawing, the lysates were cleared of debris by centrifugation at 14,000 g for 5 min at 4° C., and the resulting supernatants were stored at −70° C. Newly prepared monocyte monolayers contained no detectable levels of intracellular TNF-α.

The results are shown in Tables 3 and 4 below.

TABLE 3

TNF-α Synthesis by Human Monocytes Stimulated with Various Glucan Preparations

| Glucan | Conc. | TNF-α (pg/$10^6$ monocytes) | | | |
|---|---|---|---|---|---|
| | | 1 | 2 | 3 | Mean ± SD |
| Buffer Control | | 36 | 39 | 2 | 26 ± 21 |
| Neutral soluble glucan | 1 mg/ml | 44 | 51 | 33 | 43 ± 9 |
| Laminarin | 1 mg/ml | 372 | 324 | 227 | 308 ± 74 |
| Glucan particles | 4 × $10^7$/ml | 2129 | 1478 | 1683 | 1763 ± 333 |

TABLE 4

TNF-α Stimulation by Different Conformational Structures of Soluble β-Glucan

| Glucan | Conc. | TNF-α (pg/$10^6$ monocytes) |
|---|---|---|
| Buffer Control | 1 mg/ml | 40 |
| Laminarin | 1 mg/ml | 1312 |
| Neutral soluble glucan | 1 mg/ml | 16 |
| Peak B | 1 mg/ml | 1341 |
| Glucan Particles | 4 × $10^7$/ml | 2065 |

Table 3 shows that TNF-α was stimulated by insoluble glucan particles and by laminarin, a soluble β(1–6) and β(1–3) linked glucan. There was no stimulation of TNF-α by neutral soluble glucan. Table 4 shows similar results, but further confirms that TNF-α stimulation is dependent upon conformational structure. The neutral soluble glucan did not stimulate TNF-α while Peak B (single helical conformation) did stimulate TNF-α.

Example 5

AVIDITY OF NEUTRAL SOLUBLE GLUCAN FOR THE GLUCAN RECEPTOR

Monolayers of human monocytes, prepared on siliconized glass coverslips (Czop et al., 1978, *J. Immunol.*, 120:1132), were incubated for 18 minutes at 37° C. in a humidified 5% $CO_2$ incubator with either 0.25 ml of buffer (RPMI-Mg-HEPES) or a range of concentrations (0.1–50 µg/ml) of neutral soluble glucan. The monocyte monolayers were then washed twice with 50 ml of RPMI 1640 medium and were layered with 0.25 ml of 4.8×$10^6$/ml zymosan particles (Czop and Austen, 1985, *J. Immunol.*, 134:2588–2593). After a 30 minute incubation at 37° C., the monolayers were washed three times with 50 ml of Hank's balanced salt solution to remove noningested zymosan particles. The monolayer were then fixed and stained with Giemsa. The ingestion of zymosan particles by at least 300 monocytes per monolayer was determined by visual observation under a 1000× light microscope.

Monocyte monolayers pretreated with buffer or 50 µg/ml of neutral soluble glucan as described above were subsequently tested for their capacity to ingest IgG coated sheep erythrocytes ($E^s$IgG). After an 18 minute preincubation with the neutral soluble glucan, the monolayers were incubated with 0.25 ml of 1×$10^7$/ml $E^s$IgG for 30 minutes at 37° C., washed three times with 50 ml of Hank's balanced salt solution, treated for 4 minutes with 0.84% $NH_4Cl$ to lyse noningested $E^s$IgG, and fixed and stained as described above. The percentage of monocytes ingesting ≧1 and ≧3 $E^s$IgG was determined by counting at least 300 monocytes per monolayer.

The percent inhibition of monocyte ingestion was determined by subtracting the percentage of monocytes ingesting targets after pretreatment with the neutral soluble glucan from the percentage ingesting targets after pretreatment with buffer, dividing this number by the percentage ingesting targets after pretreatment with buffer and multiplying by 100. The data are expressed as the mean of two experiments and are reported in Table 5.

TABLE 5

Glucan-receptor Binding Capacity of Distinct Conformations of Soluble β-glucans

| Test Material | Conc. | % Inhibition |
|---|---|---|
| Buffer | — | 0% |
| Neutral soluble glucan | 50 µg/ml | 74% |
| | 500 µg/ml | 86% |
| Peak B | 50 µg/ml | 50% |
| | 500 µg/ml | 56% |

Both β-glucan preparations tested above inhibited monocyte ingestion of glucan particles demonstrating their capacity to competitively bind to the β-glucan receptor on human monocytes. Neutral soluble glucan demonstrated a higher receptor binding capacity than Peak B as indicated by the greater level of inhibition achieved at both 50 µg/ml and 500 µg/ml. This biological assay demonstrates that the neutral soluble glucan is a superior ligand for the β-glucan receptor.

Example 6

IN VITRO STIMULATION OF IL-1 AND TNF FROM HUMAN MONONUCLEAR CELLS

Venous blood was obtained from healthy male volunteers and mononuclear cells were fractionated by Ficoll-Hypaque centrifugation. The mononuclear cells were washed, resuspended in endotoxin-free RPMI-1640 culture medium ultrafiltered to remove endotoxins as described elsewhere (Dinarello et al., 1987, *J. Clin. Microbiol.* 25:1233–8) at a concentration of 5×$10^6$ cells/ml and were aliquoted into 96-well microtiter plates (Endres et al., 1989, *N. E. J. Med.* 320:265–271). The cells were then incubated with either 1 ng/ml endotoxin (lipopoly-saccharide, *E. coli* 055:B5, Sigma, St. Louis), or 10 to 1000 ng/ml PGG, at 37° C. for 24 hours in 5% $CO_2$ and then lysed by three freeze-thaw cycles (Endres et al., 1989, *N. E. J. Med.* 320:265–271). Synthesis of IL-1β and TNFα were determined by specific radioimmunoassays as described elsewhere (Lisi et al., 1987, *Lymph Res.* 6:229–244; Lonnemann et al., 1988, *Lymph. Res.* 7:75–84; Van der Meer et al., 1988, *J. Leukocycte Biol.* 43:216–223.

To determine if neutral soluble glucan could act as a priming agent for cytokine synthesis with endotoxin, a known cytokine stimulant, mononuclear cells were pre-incubated with 1, 10, and 1000 ng/ml underivatized, aqueous soluble β-glucan for 3 hours at 37° C. in 5% $CO_2$. The cells were washed to remove neutral soluble glucan and were then incubated with 1 ng/ml endotoxin as described above. IL-1β and TNFα were determined as described above.

The results are summarized in Table 6. Neutral soluble glucan used as a stimulant at doses of 10–1000 ng/ml alone did not induce increased levels of IL-1β or TNFα synthesis over the control buffer treated cells. Endotoxin LPS, a known stimulant, resulted in significantly increased levels of both cytokines. In a second phase of this experiment neutral soluble glucan was tested for its ability to act as a priming agent for cytokine synthesis. The cells from the same donors were pre-incubated with three doses of neutral soluble glucan (10–1000 ng/ml) and were then exposed to endotoxin as a co-stimulant. Neutral soluble glucan did not result in any amplification of the IL-1β and TNFα levels compared to endotoxin alone.

TABLE 6

In Vitro IL-1β and TNFα Synthesis by Human Peripheral Blood Mononuclear Cells

| Stimulant | | IL-1β (ng/ml)[1] | TNFα (ng/ml)[1] |
|---|---|---|---|
| Cells only | | <0.10 | 0.14 |
| Neutral | 10 ng/ml | 0.13 | 0.16 |
| soluble | 100 ng/ml | 0.12 | 0.16 |
| glucan | 1000 ng/ml | <0.10 | 0.14 |
| LPS | 1 ng/ml | 2.62 | 2.22 |
| LPS (1 ng/ml) + | 10 ng/ml | 2.62 | 2.25 |
| Neutral | | | |
| soluble | 100 ng/ml | 2.57 | 2.07 |
| glucan | 1000 ng/ml | 2.85 | 2.27 |

[1]Values are the mean of two donors.

Example 7

INFECTION MODEL

A sepsis model was developed in rats to characterize the efficacy of PGG glucans in protecting an immunologically intact host against serious infections, such as those which commonly occur following abdominal surgery. The rat model for intra-abdominal sepsis has been well described in the scientific literature (Onderdonk et al., 1974, Infect. Immun., 10:1256, 1259).

Groups of rats received neutral soluble glucan (100 μg/0.2 ml) or saline control (0.2 ml) intramuscularly 24 hours and 4 hours prior to infectious challenge. A defined polymicrobic infectious challenge (cecal inoculum) was placed into a gelatin capsule which was then surgically implanted into the peritoneal cavity of anesthetized rats through an anterior midline incision. The early peritonitis from this experimentally induced infection was associated with the presence of gram-negative organisms within the blood and peritoneal cavity culminating in mortality. The cecal inoculum contained an array of facultative species, such E. coli, as well as other obligate anaerobes (Streptococcus sp., Bacteroides sp., Clostridium perfringens, Clostridium ramosum, Peptostreptococcus magnus and productus, Proteus mirabilis). The animals were observed four times per day for the first 48 h and twice per day thereafter. The results are reported in Table 7.

TABLE 7

Effect of Neutral Soluble Glucan on Mortality in a Rat Model for Intra-abdominal Sepsis

| Group | Mortality (%) | P vs. Saline |
|---|---|---|
| Saline | 12/20 (60) | |
| Neutral soluble glucan | 2/10 (10) | <0.01 |

These results demonstrate that neutral soluble glucan which does not induce IL-1 and TNF protects rats from lethal bacterial challenge.

Example 8

ADMINISTRATION OF NEUTRAL SOLUBLE GLUCAN TO HUMANS

Figure 5:
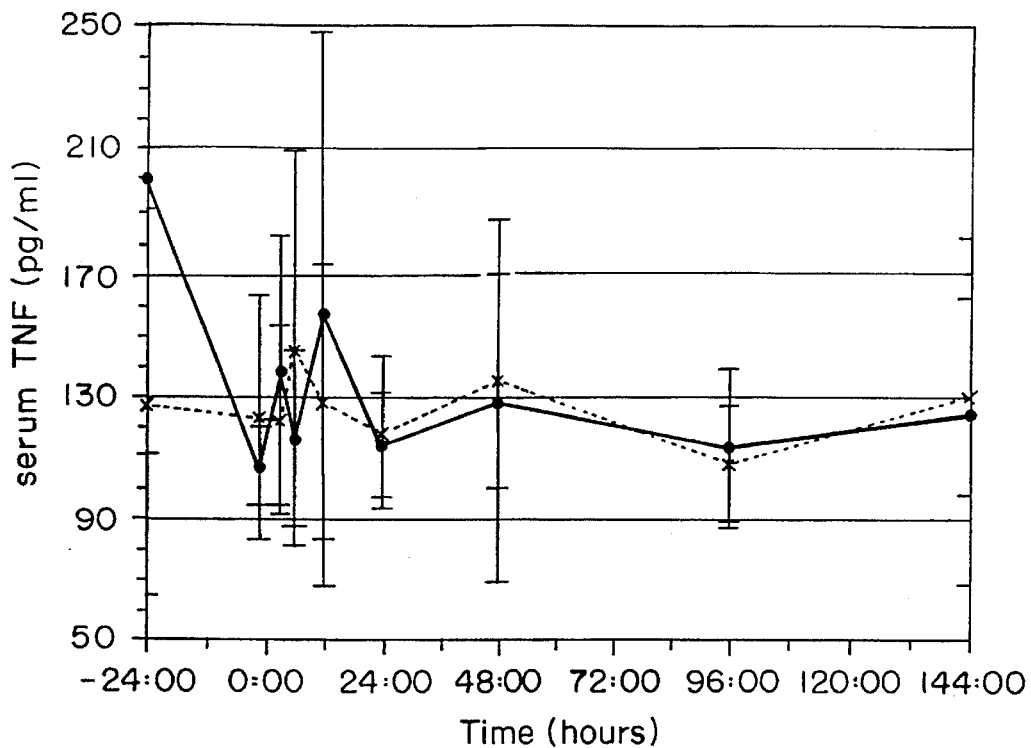
FIG. 5 shows the change in serum IL-1 levels, over time, taken from patients intravenously infused with placebo (broken line) or neutral soluble glucan (solid line).
Figure 6:
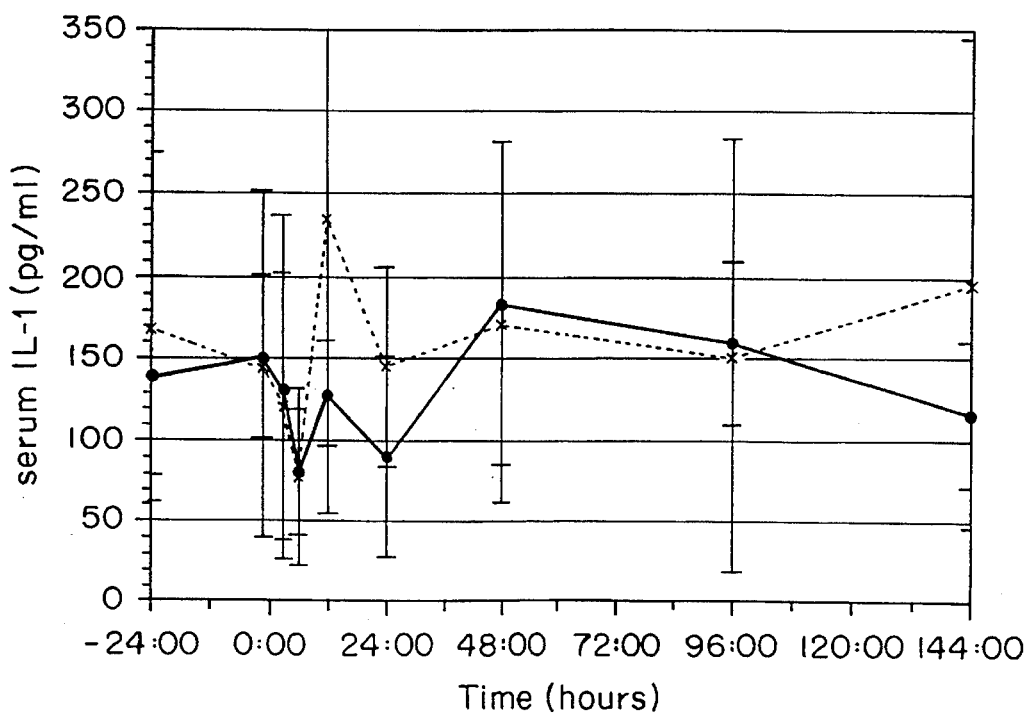
FIG. 6 shows the change in serum IL-1 levels, over time, taken from patients intravenously infused with placebo (broken line) or neutral soluble glucan (solid line).

A randomized, double-blind, placebo-controlled clinical trial was conducted on healthy males to evaluate the safety of neutral soluble glucan (2.25 mg/kg) injected by intravenous infusion compared to a placebo control. No adverse effects were observed. There was also no observed elevation in IL-1, TNF, IL-6, IL-8 and GM-CSF. Single intravenous administration of neutral soluble glucan resulted in increases in monocytes and neutrophils and in the killing activity of these cells proving that neutral soluble glucan retains the desirable immunological activities in humans. See Tables 8, 9 and 10 below. However, as shown in FIGS. 5 and 6 no changes occurred in serum IL-1 and TNF and none of the patients experienced fever or inflammatory reactions. The results are consistent with the in vitro data reported in the earlier examples.

TABLE 8

Change In Absolute Neutrophil Counts (× 1000/μl) After Neutral Soluble Glucan Administration

| Dose Level | | B | Hour 8 | Hour 12 | Hour 24 |
|---|---|---|---|---|---|
| Saline | Mean | 4.06 | 4.34 | 4.31 | 3.43 |
| | STD | 2.12 | 1.53 | 1.16 | 1.46 |
| | N | 6 | 6 | 6 | 6 |
| 2.5 mg/kg | Mean | 4.11 | 11.29* | 8.18 | 5.32 |
| Neutral | STD | 1.15 | 4.39 | 3.80 | 1.75 |
| Soluble | N | 6 | 6 | 6 | 6 |
| Glucan | | | | | |

B = Baseline measurement
*p <0.01 with respect to baseline

TABLE 9

Change in Monocyte Counts (× 1000/μl) After Soluble Neutral Glucan Administration

| Dose Level | | B | Hour 8 | Hour 12 | Hour 24 |
|---|---|---|---|---|---|
| Saline | Mean | 0.33 | 0.44 | 0.59 | 0.33 |
| | STD | 0.09 | 0.10 | 0.22 | 0.12 |
| | N | 6 | 6 | 6 | 6 |
| 2.5 mg/kg | Mean | 0.24 | 0.63* | 0.67* | 0.31 |
| Neutral | STD | 0.10 | 0.24 | 0.32 | 0.15 |
| Soluble | N | 6 | 6 | 6 | 6 |
| Glucan | | | | | |

B = Baseline measurement
*p <0.01 with respect to baseline

TABLE 10

Ex Vivo Microbicidal Activity of Normal Volunteers
Receiving Neutral Soluble Glucan
Mean Change in % Killing[1]

| Dose Level | | Hour 3 | Hour 6 | Hour 24 | Day 2 | Day 3 | Day 6 |
|---|---|---|---|---|---|---|---|
| Saline | | 0 | 0 | 0 | 0 | 0 | 0 |
| 2.5 mg/kg | Mean | 42.86 | 32.33 | 20.90 | 48.96 | 39.22 | 31.17 |
| Neutral | N | 6 | 6 | 6 | 6 | 6 | 6 |
| Soluble Glucan | p-Value | 0.062 | 0.036 | 0.300 | 0.045 | 0.085 | 0.026 |

[1]Normalized with respect to the saline control

Example 9

WOUND HEALING EFFECTS OF NEUTRAL SOLUBLE GLUCANS

Wound healing studies were performed on hairless mouse models having full thickness wounds with and without *Staphylococcus aureus* infection.

Hairless SKH-1 inbred mice (6–8 weeks of age) were anesthetized with ether and a midline 3 cm full thickness longitudinal incision was made with a number 10 scalpel blade, producing a full thickness wound that did not penetrate the underlying fascia. Incisions were closed using steel clips at 1 cm intervals.

Formulations of neutral soluble glucan in phosphate buffered saline were applied 30 minutes following wounding and reapplied at 24 hour intervals during the seven day post-operative period. Two micrograms of neutral soluble glucan/mouse per day was topically applied. Wounds were examined daily and rank-ordered for effectiveness of formulation for enhancement of visual based wound healing each day. Wounds were scored for closure on a scale of 0–5, with 5 indicating the most healing. In one group of mice that served as the infection model, the wound was treated with a culture of $10^7$ *Staphylococcus aureus* 30 minutes after wounding and 2 hrs prior to treatment with the neutral soluble glucan formulation.

Histological evaluation of the wound site of each test group was made. The dermis of the control group (untreated wound) was heavily infiltrated with both lymphocytes and monocytes/macrophages. However, re-epithelialization that occurred at the epidermal layer was incomplete. The tissue section showed that the dermal tissue was weak, in that the tissue integrity was not maintained when it was sectioned.

The histology of the wounded tissue isolated from mice treated for three days with phosphate buffered saline containing the neutral soluble glucan showed that there was a heavy infiltration of macrophages and lymphocytes. Tissue integrity was good.

When topically applied to a wound, a composition of neutral soluble glucan, stimulated white blood cell entry and activity at the wound site and accelerated wound healing within the dermal layer of the wound. Furthermore, the composition effectively eliminated infection produced by bacterial infection (*Staphylococcus aureus*) and prevented the progression to sepsis, unlike untreated wounds which progressed to sepsis.

Example 10

STIMULATION OF PLATELET PROLIFERATION

The platelet proliferation stimulatory effect of the neutral soluble glucan was tested in an animal model system following irradiation or administration of the chemotherapeutic agent cisplatin. These experiments demonstrated the unexpected platelet stimulatory effect.

Figure 7:
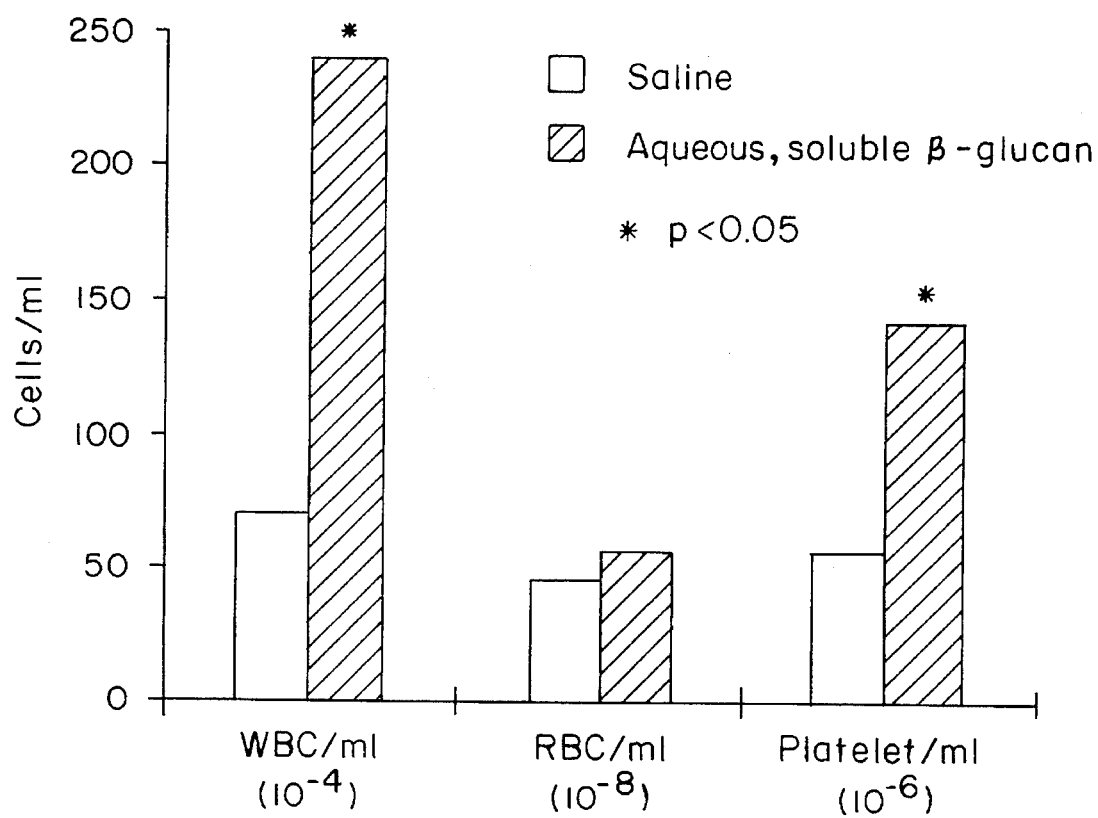
FIG. 7 is a diagram representing peripheral blood counts from irradiated mice following administration of neutral soluble glucan.

More specifically, neutral soluble glucan prepared as described in Example 1 was administered to groups of 10 mice in a single IV bolus 20 hours prior to radiation exposure. Mice were bilaterally exposed to a total-body irradiation of 7.5-Gy. Fourteen days after irradiation the mice were sacrificed and whole blood samples were analyzed for peripheral blood counts. As shown in FIG. 7, the platelet cell count was increased nearly 3-fold relative to saline treated control levels.

Figure 8:
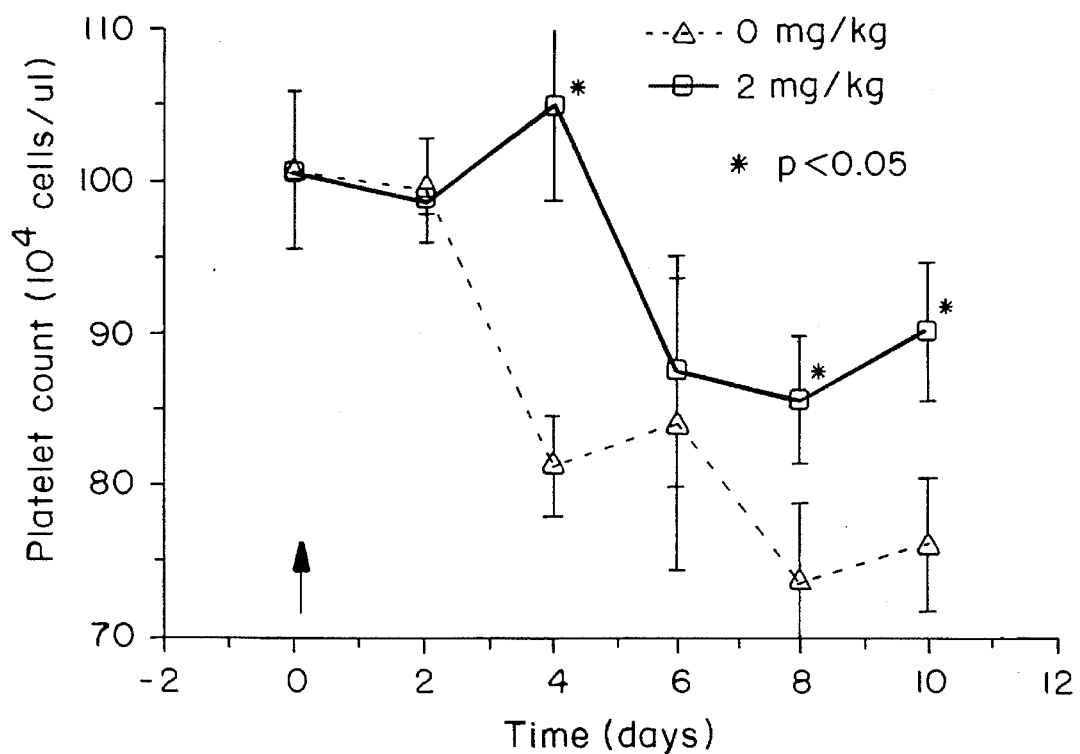
FIG. 8 is a diagram representing platelet cell counts from cisplatin-treated mice following administration of neutral soluble glucan.

In addition to tests on irradiated mice, cisplatin treated mice were also tested for the effect of the neutral soluble glucan on platelet hematopoiesis. Balb/c mice were injected intravenously with cisplatin at a dose of 9.3 mg/kg through the tail vein one hour before injecting the neutral soluble glucan, prepared as described in Example 1, intramuscularly in a single dose of 0 (saline) or 2 mg/kg on day 0. Platelet counts were determined before treatment (day 0) and at 2, 4, 6, 8, and 10 days post-treatment. The results of this experiment are shown in FIG. 8. Each data point represents the mean and standard error of platelet counts from five mice. The statistically significant differences between the saline and underivatized, aqueous soluble β-glucan (2 mg/kg) are noted: *$p<0.05$.

Biological Deposit

*Saccharomyces cerevisiae* strain R4 Ad was deposited on Aug. 20, 1992 with the American Type Culture Collection (ATCC), 12301 Parklawn Drive, Rockville, Md., under the terms of the Budapest Treaty. The strain has been assigned ATCC accession number 74/81. Upon issuance of a patent, this deposit will be irrevocable.

Equivalents

Those skilled in the art will recognize or be able to ascertain, using no more than routine experimentation, many equivalents to the specific materials and components described herein. Such equivalents are intended to be encompassed in the scope of the following claims:

We claim:

1. A method for stimulating platelet proliferation comprising administering to an animal or human a platelet stimulating amount of an underivatized, aqueous soluble β(1–3) glucan in a triple helix conformation.

2. The method of claim 1 wherein the glucan is derived from yeast.

3. The method of claim 2 wherein the yeast is a strain of *Saccharomyces cerevisiae*.

4. The method of claim 3 wherein the strain of *Saccharomyces cerevisiae* is strain R4 (NRRL Y-15903) or strain R4 Ad (ATCC 74181).

5. The method of claim 1 wherein the glucan is formulated into a composition comprising the glucan and a physiologically acceptable vehicle.

6. The method of claim 5 wherein the physiologically acceptable vehicle is water, sterile saline, phosphate buffered saline, isotonic saline or dextrose.

7. The method of claim 5 wherein the concentration of glucan in the physiologically acceptable vehicle is from about 0.5 to about 100 mg/ml.

8. The method of claim 5 wherein the composition is in the form of a liquid, tablet, capsule, powder or solution.

9. A method for stimulating platelet proliferation comprising administering to an animal or human a platelet stimulating amount of an underivatized, aqueous soluble β(1–3) glucan in a triple helix conformation having immunostimulating properties, wherein the soluble glucan when intravenously injected into a human will not stimulate or prime the production of interleukin-1 or tumor necrosis factor or both, in the serum of said human.

10. The method of claim 9 wherein the glucan is derived from yeast.

11. The method of claim 10 wherein the yeast is a strain of *Saccharomyces cerevisiae*.

12. The method of claim 11 wherein the strain of *Saccharomyces cerevisiae* is strain R4 (NRRL Y-15903) or strain R4 Ad (ATCC 74181).

13. The method of claim 9 wherein the glucan is formulated into a composition comprising the glucan and a physiologically acceptable vehicle.

14. The method of claim 13 wherein the physiologically acceptable vehicle is water, sterile saline, phosphate buffered saline, isotonic saline or dextrose.

15. The method of claim 13 wherein the concentration of glucan in the physiologically acceptable vehicle is from about 0.5 to about 100 mg/ml.

16. The method of claim 13 wherein the composition is in the form of a liquid, tablet, capsule, powder or solution.

17. A method for stimulating platelet proliferation comprising administering to an animal or human a platelet stimulating amount of an underivatized, aqueous soluble β(1–3) glucan in a triple helix conformation having an average molecular weight of from about 30,000 to about 500,000 daltons.

18. The method of claim 17 wherein the glucan is formulated into a composition comprising the glucan and a physiologically acceptable vehicle.

19. The method of claim 18 wherein the physiologically acceptable vehicle is water, sterile saline, phosphate buffered saline, isotonic saline or dextrose.

20. The method of claim 18 wherein the concentration of glucan in the physiologically acceptable vehicle is from about 0.5 to about 100 mg/ml.

21. The method of claim 18 wherein the composition is in the form of a liquid, tablet, capsule, powder or solution.

22. The method of claim 17 wherein the glucan is derived from yeast.

23. The method of claim 22 wherein the yeast is a strain of *Saccharomyces cerevisiae*.

24. The method of claim 23 wherein the strain of *Saccharomyces cerevisiae* is strain R4 (NRRL Y-15903) or strain R4 Ad (ATCC 74181).

25. A method for stimulating platelet proliferation comprising administering to an animal or human a platelet stimulating amount of an underivatized, aqueous soluble β(1–3) glucan in a triple helix conformation having immunostimulating properties and when analyzed by gel permeation undergoes a conformational transition from a multiple helix at pH 7 to a single helical conformation at pH 13.

26. The method of claim 25 wherein the glucan is derived from yeast.

27. The method of claim 27 wherein the yeast is a strain of *Saccharomyces cerevisiae*.

28. The method of claim 27 wherein the strain of *Saccharomyces cerevisiae* is strain R4 (NRRL Y-15903) or strain R4 Ad (ATCC 74181).

29. The method of claim 25 wherein the glucan is formulated into a composition comprising the glucan and a physiologically acceptable vehicle.

30. The method of claim 25 wherein the physiologically acceptable vehicle is water, sterile saline, phosphate buffered saline, isotonic saline or dextrose.

31. The method of claim 25 wherein the concentration of glucan in the physiologically acceptable vehicle is from about 0.5 to about 100 mg/ml.

32. The method of claim 25 wherein the composition is in the form of a liquid, tablet, capsule, powder or solution.

* * * * *

UNITED STATES PATENT AND TRADEMARK OFFICE
CERTIFICATE OF CORRECTION

PATENT NO. : 5,532,223
DATED : July 2, 1996
INVENTOR(S) : Spiros Jamas, D. Davidson Easson, Jr. and Gary R. Ostroff It is certified that error appears in the above-indentified patent and that said Letters Patent is hereby corrected as shown below:

In Column 10, line 2, delete "vital" and insert ---viral---.

In Claim 27, Column 22, line 25, delete "27" and insert ---26---.

Signed and Sealed this

First Day of October, 1996

Attest:

BRUCE LEHMAN

Attesting Officer

Commissioner of Patents and Trademarks